(12) United States Patent
Stern et al.

(10) Patent No.: US 7,107,097 B2
(45) Date of Patent: Sep. 12, 2006

(54) ARTICULATED NEURAL ELECTRODE ASSEMBLY

(75) Inventors: Corrinne Stern, Kent, WA (US); Amy C. Kinsella, Seattle, WA (US); Bradford C. Fowler, Duvall, WA (US); Allen Wyler, Seattle, WA (US)

(73) Assignee: Northstar Neuroscience, Inc., Seattle, WA (US)

( * ) Notice: Subject to any disclaimer, the term of this patent is extended or adjusted under 35 U.S.C. 154(b) by 0 days.

(21) Appl. No.: 10/707,818

(22) Filed: Jan. 14, 2004

(65) Prior Publication Data

US 2005/0154435 A1 Jul. 14, 2005

(51) Int. Cl.
*A61N 1/00* (2006.01)

(52) U.S. Cl. .......................... 607/2; 607/116; 607/152; 600/378

(58) Field of Classification Search ................. 607/129, 607/115, 116, 148, 149, 152, 139; 600/373–381
See application file for complete search history.

(56) References Cited

U.S. PATENT DOCUMENTS

| | | | | |
|---|---|---|---|---|
| 4,102,331 A | * | 7/1978 | Grayzel et al. | 600/385 |
| 4,233,987 A | * | 11/1980 | Feingold | 600/382 |
| 4,522,211 A | * | 6/1985 | Bare et al. | 600/392 |
| 4,903,702 A | * | 2/1990 | Putz | 600/377 |
| 5,133,356 A | * | 7/1992 | Bryan et al. | 600/392 |
| 5,215,087 A | * | 6/1993 | Anderson et al. | 600/392 |
| 5,445,537 A | * | 8/1995 | Abyzov | 439/449 |
| 5,772,591 A | | 6/1998 | Cram | |
| 5,846,217 A | * | 12/1998 | Beck et al. | 604/20 |
| 6,301,493 B1 | | 10/2001 | Marro et al. | |
| 6,782,293 B1 | * | 8/2004 | Dupelle et al. | 607/142 |
| 2002/0128700 A1 | * | 9/2002 | Cross, Jr. | 607/117 |
| 2004/0093051 A1 | | 5/2004 | Chinn et al. | |
| 2004/0243205 A1 | | 12/2004 | Keravel et al. | |

* cited by examiner

*Primary Examiner*—Mark Bockelman
(74) *Attorney, Agent, or Firm*—Sonya C. Harris; Leif R. Sloan

(57) ABSTRACT

Apparatuses, devices, and/or systems that may be configured for placement at one or more cortical and/or other neuroanatomical sites to provide electrical stimulation and/or monitor neuroelectric activity within a patient. In one embodiment, an implantable articulated electrode assembly may include an array of electrodes or electrical contacts carried by a support member configured to be implanted or positioned relative to a set of neuroanatomical sites. Various embodiments of the articulated electrode assemblies may comprise multiple portions, segments, paddles, and/or panels having spatially divergent placement capabilities in relation to one another. Such segments or panels may be positioned in a variety of manners relative to each other and/or one or more neuroanatomical sites or locations, which may facilitate establishment of an intended type of stimulation field distribution and/or monitoring configuration.

26 Claims, 20 Drawing Sheets

TO POWER SOURCE

ARTICULATED NEURAL ELECTRODE ASSEMBLY

CROSS REFERENCE TO RELATED APPLICATIONS

This disclosure relates to and incorporates by reference U.S. Application No. 60/482,937, entitled "Apparatuses and Systems for Applying Electrical Stimulation to a Patient," filed on Jun. 26, 2003.

BACKGROUND OF INVENTION

The following disclosure is related to systems and methods for applying neural stimulation to and/or receiving neural signals from a patient, for example, at a surface site on or proximate to the patient's cortex.

A wide variety of mental and physical processes are controlled or influenced by neural activity in particular regions of the brain. The neural functions in some areas of the brain (e.g., the sensory or motor cortices) are organized according to physical or cognitive functions. Several other areas of the brain also appear to have distinct functions in most individuals. In the majority of people, for example, the occipital lobes relate to vision, the left interior frontal lobes relate to language, and the cerebral cortex appears to be involved with conscious awareness, memory, and intellect.

Many problems or abnormalities can be caused by damage, disease, and/or disorders of the brain. Effectively treating such abnormalities may be very difficult. For example, a stroke is a common condition that damages the brain. Strokes are generally caused by emboli (i.e., obstruction of a blood vessel), hemorrhages (i.e., rupture of a blood vessel), or thrombi (i.e., clotting) in the vascular system of a specific region of the brain. Such events generally result in a loss or impairment of neural function (e.g., neural functions related to facial muscles, limbs, speech, etc.). Stroke patients are typically treated using physical therapy that attempts to rehabilitate the loss of function of a limb or another affected body part. Stroke patients may also be treated using physical therapy plus an adjunctive therapy such as amphetamine treatment.

As another example, Parkinson's Disease (PD) is related to the degeneration or death of dopamine producing neurons in the substantia nigra region of the basal ganglia in the brain. As the neurons in the substantia nigra deteriorate, the reduction in dopamine causes abnormal neural activity that results in a chronic, progressive deterioration of motor function control and possibly other symptoms.

Neural activity in the brain can be influenced by electrical energy supplied from an external source such as a waveform generator. Various neural functions can be promoted or disrupted by applying an electrical current to the cortex or other region of the brain. As a result, researchers have attempted to use electrical or magnetic stimulation signals to control or affect brain functions. Electrical stimulation signals may comprise a series of electrical pulses that can affect neurons within a target neural population. Stimulation signals may be defined or described in accordance with stimulation signal parameters that include pulse amplitude, pulse frequency, stimulation signal duration, and/or other parameters.

In certain applications, such as deep brain stimulation, electrical stimulation is provided by a pulse system coupled to a plurality of therapy electrodes or electrical contacts. The pulse system is typically implanted into a patient at a subclavicular location, and the therapy electrodes can be implanted into the patient at a target site for stimulating the desired neurons.

FIG. 1 is a perspective view of an implantable electrode assembly 10 configured in accordance with the prior art. The electrode assembly 10 can be a Resume II electrode assembly provided by Medtronic, Inc., of 710 Medtronic Parkway, Minneapolis, Minn. 55432-5604. The electrode assembly 10 includes a plurality of plate electrodes 14a–d carried by a flexible substrate 12. A polyester mesh 11 is molded into the substrate 12 to increase the tensile strength of the substrate 12. A cable 16 houses four individually insulated leads 18a–d that extend into the substrate 12. A connector 20 joins with the receptacle 22 to form a coupling between the electrode assembly 10 and a power source (not shown).

One problem of using an electrode assembly 10 of the type shown in FIG. 1 is acquiring an appropriate placement at or upon a stimulation site. Certain obstacles may hinder an appropriate placement of conventional electrodes. In the case of stimulation in or upon the brain, the brain's anatomical structure may naturally render electrode placement upon the brain's surface a complicated undertaking. The brain is replete with convolutions and crevices, which may impede electrode placement at specific locations.

Furthermore, in some instances, brain damage or degeneration may cause an infarct or tissue atrophy, which may alter neural topography in the damaged region or area. Physically damaged tissue in a given region may alter neural topography in surrounding regions, further causing impediments to electrode placement. Thus, the presence of brain damage or degeneration may complicate electrode placement relative to obtaining an intended therapeutic outcome.

Another problem associated with using a conventional electrode 10 is that in certain situations, the electrode's structure itself may limit manners in which neural stimulation can be applied or delivered to a target neural population. In particular, an electrode 10 having a structure of the type shown in FIG. 1A may be significantly limited with respect to an extent to which an electric field distribution can be configured relative to a given target neural population. This may result in decreased neural stimulation efficacy, and/or other problems such as insufficient surface-to-contact coupling, unpredictable impedance, current leakages, unregulated stimulation parameters, elevated power consumption and shorter battery life. Moreover, placement of the therapy electrodes on an appropriate anatomical location for effectuating desired therapeutic results may be difficult and time consuming. There is a significant need to improve procedures for appropriately placing electrode devices at a desired treatment site.

DETAILED DESCRIPTION

Figure 1:
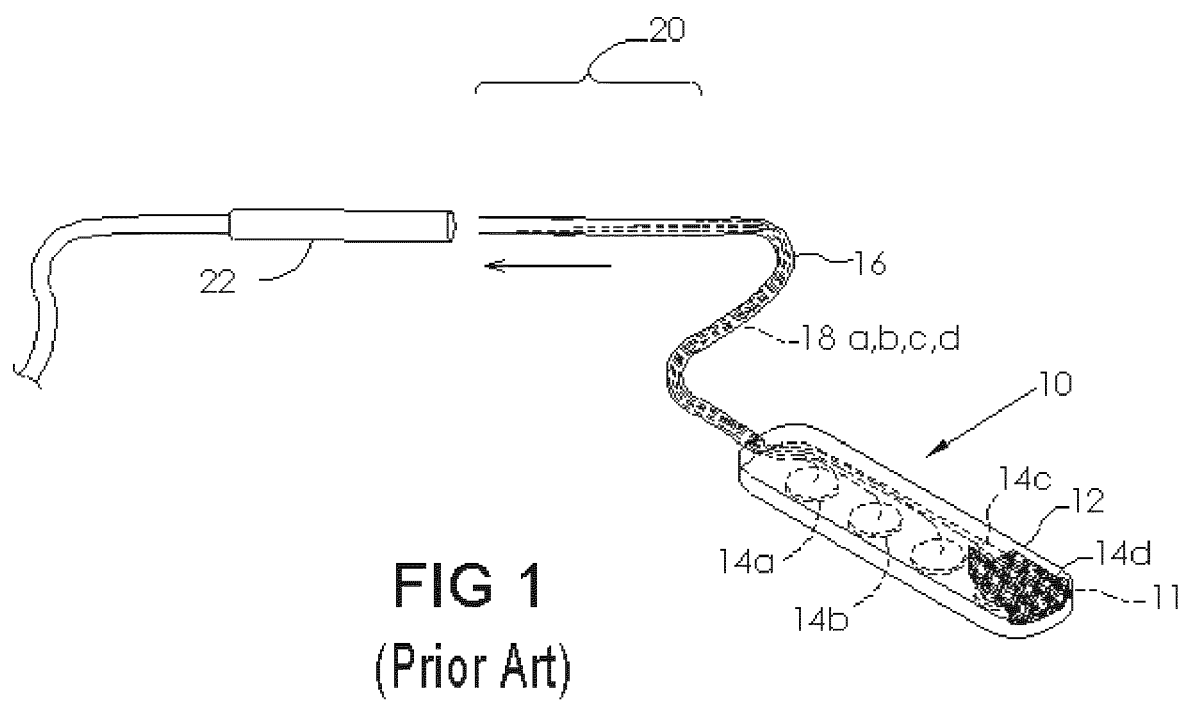
FIG. 1 is a perspective view of an implantable electrode assembly configured in accordance with the prior art.

The present disclosure describes various embodiments of apparatuses, devices, and/or systems that may be configured to apply or deliver neural stimulation to a patient, for example, at one or more cortical and/or other neuroanatomical sites; and associated procedures directed toward the use of such apparatuses, devices, and/or systems. Depending upon embodiment details, one or more portions of apparatuses and/or systems described herein may alternatively or additionally be configured to sense or monitor neuroelectric activity within a patient, for example, at one or more cortical and/or other neuroanatomical sites.

Stimulation systems and/or methods described herein may be used to treat a variety of neurological conditions and/or neurologic deficits associated with, for example, stroke, cerebral palsy, multiple sclerosis, movement disorders such as Parkinson's Disease, and/or neuropsychiatric disorders such as depression. Depending on the nature of a particular condition, neural stimulation applied or delivered in accordance with various embodiments of such systems and/or methods may alleviate one or more patient symptoms and/or may facilitate or effectuate reorganization of interconnections or synapses between neurons to (a) provide at least some degree of recovery of a lost function; and/or (b) develop one or more compensatory mechanisms to at least partially overcome a functional deficit. Such reorganization of neural interconnections may be achieved, at least in part, by a change in the strength of synaptic connections and/or effectuated through a process that corresponds to a mechanism commonly known as Long-Term Potentiation (LTP). Electrical stimulation applied to one or more target neural populations either alone or in conjunction with behavioral activities and/or adjunctive or synergistic therapies may facilitate or effectuate neural plasticity and the reorganization of synaptic interconnections between neurons.

Certain specific details are set forth in the following description, and in FIGS. 2A through 12, to provide a thorough understanding of various embodiments of the invention. Other details describing structures and systems well known to those of ordinary skill in the relevant art are not set forth in the following description, however, to avoid unnecessarily obscuring the description of various embodiments of the invention. Dimensions, angles, and other specifications shown in the following figures are merely illustrative of particular embodiments of the invention. Accordingly, other embodiments can have other dimensions, angles, and specifications without departing from the spirit or scope of the invention. In addition, still other embodiments of the invention can be practiced without several of the details described below. In the figures, identical reference numbers identify identical or at least generally similar elements. Additionally, a given reference number followed by an identifying letter may correspond to a specific embodiment, while such a reference number when used without an identifying letter may correspond to several related or generally related embodiments.

Figure 2A:
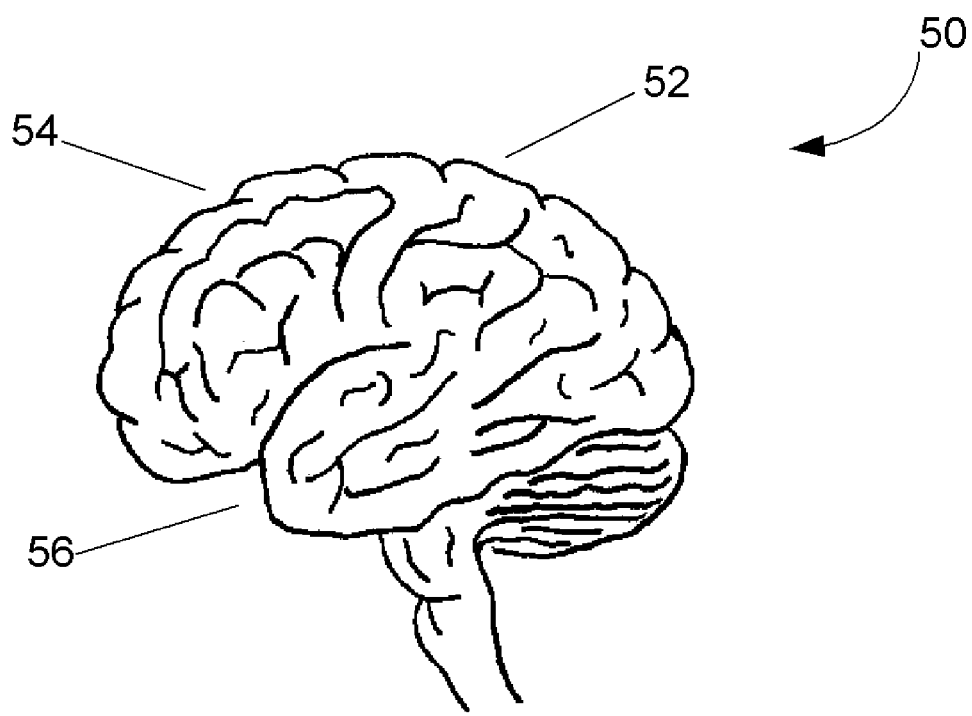
FIG. 2A is a lateral view of the brain illustrating the motor cortex, the limbic association area, and the anterior association area.

FIG. 2A is a lateral view of the brain 50 illustrating the motor cortex 52, the limbic association area 54, and the anterior association area 56. The motor cortex 52 is concerned with movements of the face, neck and trunk, arms and legs. The motor cortex 52 affects motor neurons affecting the skeletal musculature and is essential for the capacity to perform finely graded movements of the arms and legs. The anterior association area 56, also known as the prefrontal cortex, is concerned with planning movement. The limbic association area 54 is concerned with emotion and memory storage.

Figure 2B:
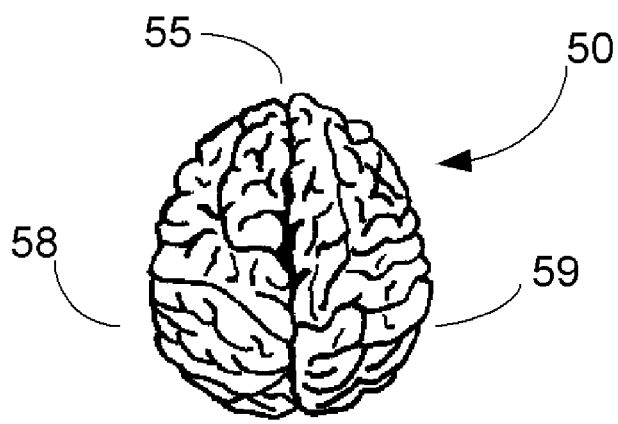
FIG. 2B is a top view of the brain showing the interhemispheric fissure and the two hemispheres of the brain.

FIG. 2B is a top view of the brain 50 showing the interhemispheric fissure 55 and the two hemispheres 58, 59 of the brain 50. Neural stimulation in association with particular embodiments of the invention may involve stimulation of one or more portions of one or more neural areas or regions either sequentially or simultaneously. In certain embodiments, bilateral stimulation may be desirable wherein electrodes may be placed upon, along, and/or between particular areas of both hemispheres 58, 59. Such areas may be neurofunctionally distinct, generally distinct, and/or homotypic. Neural sensing or monitoring in association with particular embodiments of the invention may involve considerations analogous or similar to those described above.

The effectiveness of a neural stimulation procedure may be related to an electric field distribution produced by or associated with an electrode employed in the procedure. In general, the electric or stimulation field distribution depends upon a) electrode design; b) the particular electrical contacts to which electrical stimulation signals are applied; and c) the magnitudes and polarities of applied stimulation signals. An electrode's design may encompass the structure and spatial organization of its contacts, the as-manufactured electrical couplings thereto, and/or other factors.

In order to increase or maximize a likelihood that neural stimulation will be effective, electrode placement or positioning procedures should facilitate the generation of an intended or desired type of stimulation field distribution. Various embodiments of electrode assemblies described herein may comprise multiple portions, segments, panels, and/or panels having spatially divergent placement capabilities in relation to one another. Such segments or panels may be placed or positioned in a variety of manners relative to each other and/or one or more neuroanatomical sites or locations, which may facilitate the generation of an intended type of stimulation field distribution.

FIGS. 3A–6 illustrate particular embodiments of articulated neural electrode assemblies 100 (shown as 100A–E). Depending upon embodiment details, an electrode assembly 100 may include an array of electrodes or electrical contacts 110 carried by a support member 120 configured to be implanted and positioned or placed relative to a set of neuroanatomical sites, as further detailed below. A neuroanatomical site may be a stimulation site and/or a sensing or monitoring site. As used herein, the terms "stimulation site" and/or "monitoring site" refer to an anatomical location where one or more portions of an articulated neural electrode assembly 100 or electrical contacts 110 associated therewith may be placed. For example, in certain embodiments, one or more stimulation and/or monitoring sites may be proximate to the cortex, either upon or beneath the dura mater. Depending upon embodiment details, a stimulation site may also be a monitoring site.

Figure 3A:
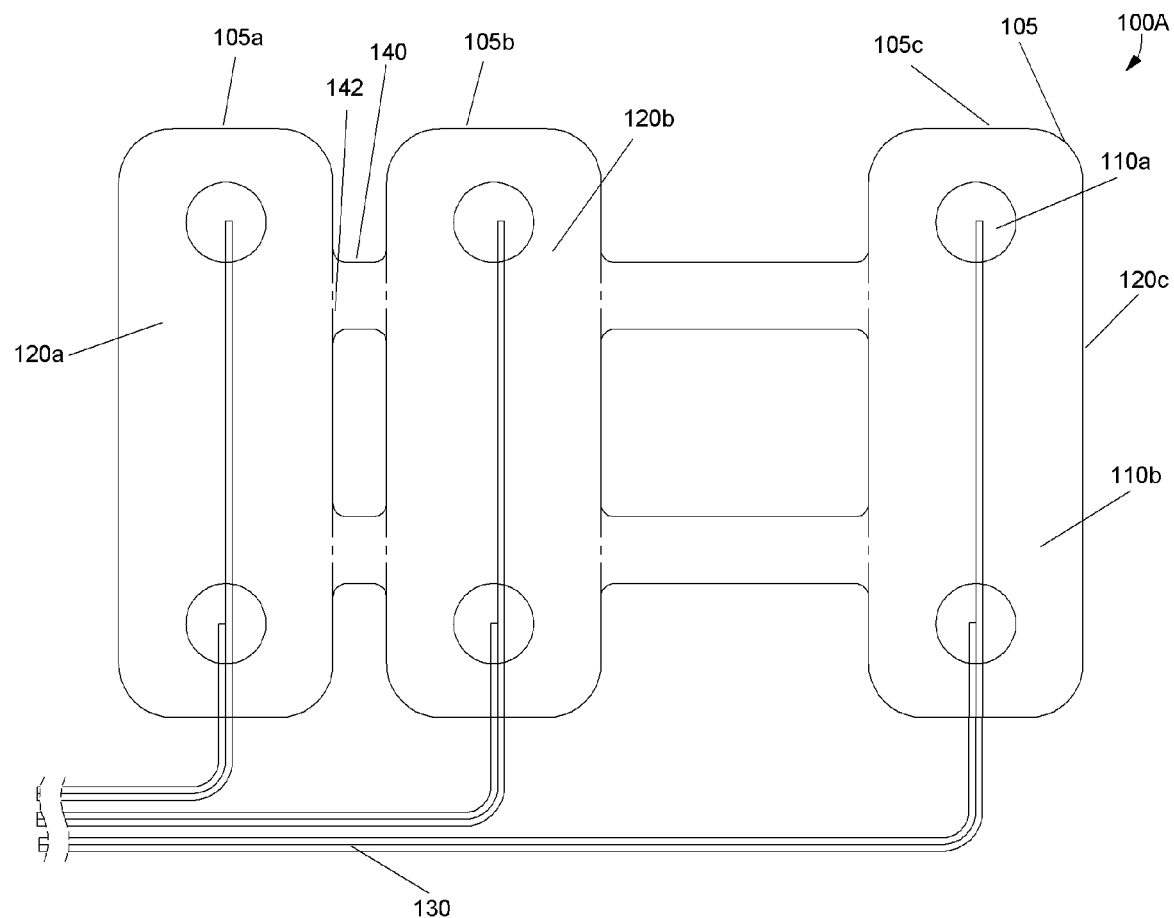
FIG. 3A is a plan view of an articulated neural electrode assembly in accordance with an embodiment of the invention.

FIG. 3A is a plan view of an articulated neural electrode assembly 100A according to an embodiment of the invention. In one embodiment, the electrode assembly 100A comprises a set of selectively separable or discontinuous paddles, multi-segmented grids, electrode arrays, and/or panels 105; a set of coupling members 140 configured to couple panels 105 in a separable, detachable, severable, and/or removable manner; and a set of electrical leads or lead wires 130 configured to couple the panels 105 to a power source (not shown). Although three panels 105a–c are illustrated, it is to be appreciated that fewer or additional panels 105 may be employed depending upon embodiment details. One or more panels 105 may be of a contoured shape. Herein, contoured may be construed as having one or more rounded or curvaceous corners, edges and/or peripheries. A contoured shape may facilitate panel placement and may increase a manner in which any given panel 105 conforms and/or adheres to a surface of a stimulation site.

Each panel 105 may comprise a support member 120 that carries a set of electrical contacts 110 and possibly a portion of one or more electrical leads 130 coupled to such contacts 110. A support member 120 may comprise one or more biologically compatible materials suitable for implantation, for example, a Silicone-based and/or other type of low durometer material. Low durometer materials may provide flexibility and pliability, which may facilitate conformity and/or placement to neural topography at any given stimulation/monitoring site.

Referring again to FIGS. 2A and 2B, the brain is replete with neuroanatomical irregularities, which may include various irregular, nonuniform, curved, and/or uneven surfaces, shapes, and/or recesses. Various embodiments of articulated electrode assemblies 100 may facilitate flexible and/or enhanced accuracy positioning and/or improved conformity of one or more panels 105 and/or electrical contacts 110 relative to such irregularities. Other neural tissue and/or regions (e.g., the spinal cord) may be associated with anatomical structures (e.g., vertebra within the spinal column) that complicate and/or partially obstruct access to targeted neural tissue. Various embodiments of articulated electrode assemblies 100 may aid the selective positioning and/or conformity of one or more panels 105 and/or electrical contacts 110 upon or proximate to targeted neural tissue relative to other anatomical structures. In general, one or more panels 105 may be dimensioned in a manner that corresponds to a type of neural region and/or structure that such panels 105 may be expected to stimulate and/or monitor. Although a panel 105 may be of essentially any shape, in certain embodiments, a panel 105 may have a length ranging between approximately 15 mm 50 mm, and/or a thickness ranging between approximately 0.3 mm 2 mm, and/or a minimum width of approximately 7 mm. In other embodiments, one or more panels 105 may have similar or different dimensions. As a result of the foregoing, an articulated electrode assembly 100 may improve neural stimulation and/or monitoring efficacy, and/or increase a likelihood of realizing an intended neural stimulation and/or monitoring result.

Referring again to FIG. 3A, a support member 120 may comprise a single layer of material, or a multiple layer structure or sandwich. Depending upon embodiment details, each panel 105 may be formed from an individual support member 120; or multiple panels 105 may be formed from a single support member 120 that is shaped or manufactured in accordance with a desired number of panels 105.

Each contact 110 may comprise a biologically compatible electrically conductive material, for example, stainless steel, Gold, or Platinum-Iridium. One or more contacts 110 may be coupled to a particular lead wire 130 to facilitate contact biasing at a given potential. In certain embodiments, a signal polarity associated with one or more contacts 110 may be specified at one or more stimulation and/or monitoring sites, possibly in a selective manner. For example, particular contacts 110 may be biased in accordance with a bipolar and/or unipolar polarity scheme, possibly in a time dependent manner. Such biasing flexibility may facilitate or effectuate an intended type of neural stimulation and/or monitoring result.

In various embodiments, a lead wire 130 may comprise a coil, and/or another type of wire and/or wire arrangement. Depending upon embodiment details, a lead wire 130 may range in length from approximately 10 cm to 110 cm. In certain embodiments, a lead wire 130 may have a length that falls outside such range. A lead wire 130 may be coupled to a contact 110 in a variety of manners, for example, through one or more welds. While two electrical contacts 110a–b are shown on each panel 105 in FIG. 3A, any given panel 105 may be dimensioned to carry additional or fewer electrical contacts 110 depending upon embodiment details and/or an intended type of neural stimulation and/or neural sensing or monitoring situation under consideration.

A set of coupling members 140 may couple adjacent panels 105 to one another in a separable, detachable, severable, and/or removable manner. In one embodiment, two coupling members 140 span each pair of panels 105. Other embodiments may rely upon additional or fewer coupling members 140 between each or any given pair of panels 105, for example, a single coupling member 140 between a first pair of panels 105, and two or three coupling members between a second pair of panels 105. One or more coupling members 140 may be removably coupled to a peripheral portion of one or more panels 105, such as by way of a perforated section 142.

Although a rectilinear strip is illustrated as a coupling member shape, it is to be appreciated that essentially any shape may be employed as long as the coupling members 140 span a set of panels 105. The length of one or more coupling members 140 may be established by an expected placement of panels 105 relative to one or more stimulation and/or monitoring sites and/or neural topography associated with such sites. Therefore, an initial distance between one or more panels 105 prior to their separation may vary based on an intended panel placement.

The electrode assembly 100A of FIG. 3A is described and shown with the panels 105 being laterally coupled to one another; however, without departing from the scope of the invention, it is to be appreciated that other embodiments may employ or include other geometric panel orientations. Moreover, the individual dimensions of one or more panels 105 may vary relative to one another. A number of electrical contacts 110 being carried by any given panel 105 may also vary depending on a size and/or shape of the panel 105 and/or a size and/or shape of the contact 110. In certain embodiments, one or more contacts 110 may have a diameter ranging between approximately 3 7 mm. In other embodiments, one or more contacts 110 may have similar or different diameters or dimensions.

Figure 6:
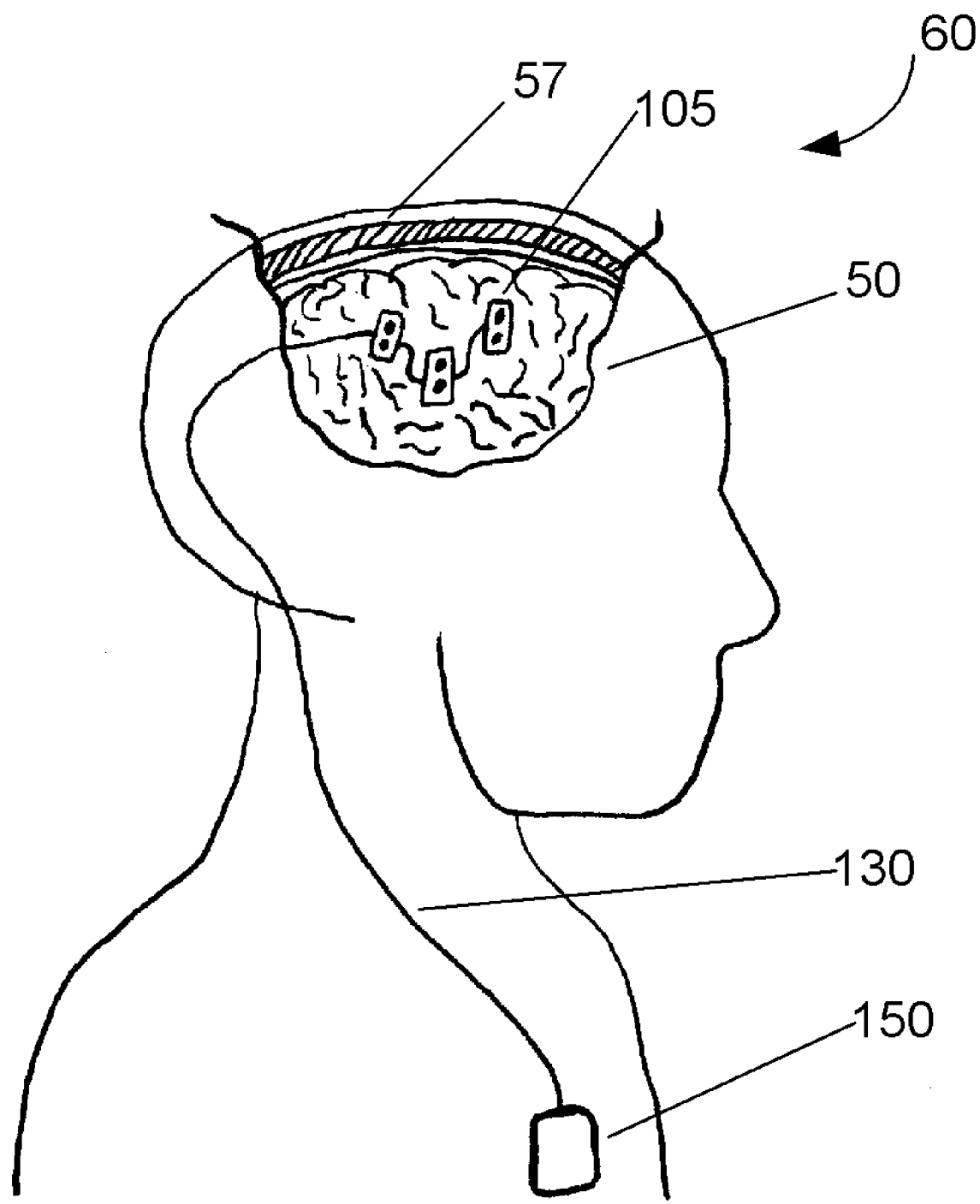
FIG. 6 is an illustration of an articulated neural electrode assembly implanted in a patient.

Referring also now to FIG. 6, an illustration of an articulated neural electrode assembly 100 implanted in a patient 60 is shown. In one embodiment, one or more lead wires 130 may couple the electrode assembly 100 to an implantable pulse generator (IPG) 150. In another embodiment, one or more lead wires 130 may couple the electrode assembly 100 to a monitoring device, such as an electroencephalogram (EEG) system (not shown). In yet another embodiment, an IPG 150 may itself be capable of both electrical stimulation and EEG monitoring.

An IPG 150 may be surgically implanted within the patient 60 in a subclavicular location. Alternatively, the IPG 150 may be surgically implanted above the patient's neck, for example, relative to a skull location posterior to the patient's ear and/or proximate to an articulated neural electrode assembly implantation site. A surgically formed tunnel or path may route the lead wires 130 to the IPG 150, in a manner understood by those skilled in the art. Depending upon embodiment details, one or more electrically conductive portions of the IPG's housing may serve as a return electrode for electrical current. In another embodiment, lead wires 130 may couple an electrode assembly 100 to a pulse generator external to the patient 60.

An articulated electrode assembly 100 may be configured for spatially divergent placement of one or more panels 105 in relation to one another at one or more stimulation and/or monitoring sites. A surgeon may remove, detach, and/or sever particular coupling members 140 to facilitate placement of one or more panels 105 at particular stimulation and/or monitoring sites within the patient 60. For example, for an articulated electrode assembly 100 having three panels 105a–c, a surgeon may position a first panel 105a upon or proximate to the patient's motor cortex; a second panel 105b upon or proximate to the patient's dorsolateral prefrontal cortex; and possibly a third panel 105c upon or proximate to another neural area or region within the patient 60. Such a panel configuration may be appropriate, for example, for treating a Parkinson's Disease patient having both motor and cognitive symptoms. As another example, a surgeon may position a first set of panels 105a–b upon or proximate to the patient's motor cortex; and a second set of panels 105c upon or proximate to the patient's premotor cortex, supplementary motor cortex, somatosensory cortex, or prefrontal cortex. In general, the nature of a patient's condition may influence or determine an appropriate type of articulated electrode 100 (e.g., one having a particular number of panels 105 and/or particular panel shape(s)) and/or panel placement suitable for the patient.

Figure 3B:
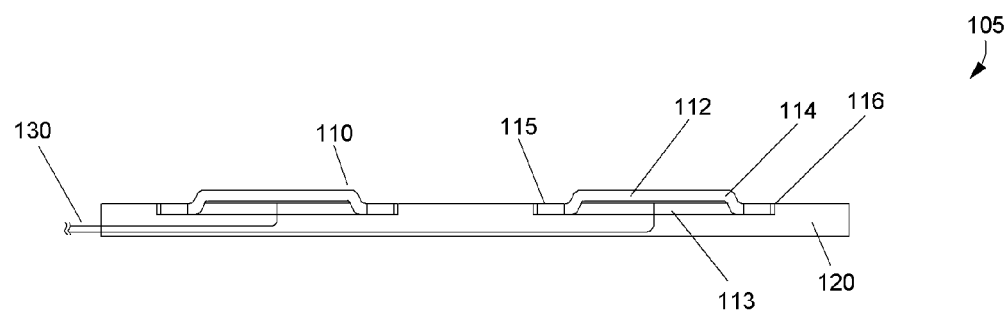
FIG. 3B is a cross-sectional view of a panel of an articulated neural electrode assembly according to an embodiment of the invention.

FIG. 3B is a cross sectional view of a panel 105 according to an embodiment of the invention. In the embodiment shown, each contact 110 may be coupled to a lead wire 130. In certain embodiments, multiple contacts may be coupled to a single lead wire 130. Alternatively, each contact 110 may be coupled to an electrically distinct lead wire 130, which may facilitate independent contact biasing. For a series of panels 105a–c, independent biasing may facilitate flexibility in establishing and/or varying potentials within any group of electrical contacts 110 as desired to specifically tailor neural stimulation and/or monitoring in accordance with particular treatment schemes and/or stimulation and/or monitoring sites. This may allow and/or provide for establishment or manipulation of electrical fields with significant flexibility.

Figure 4:
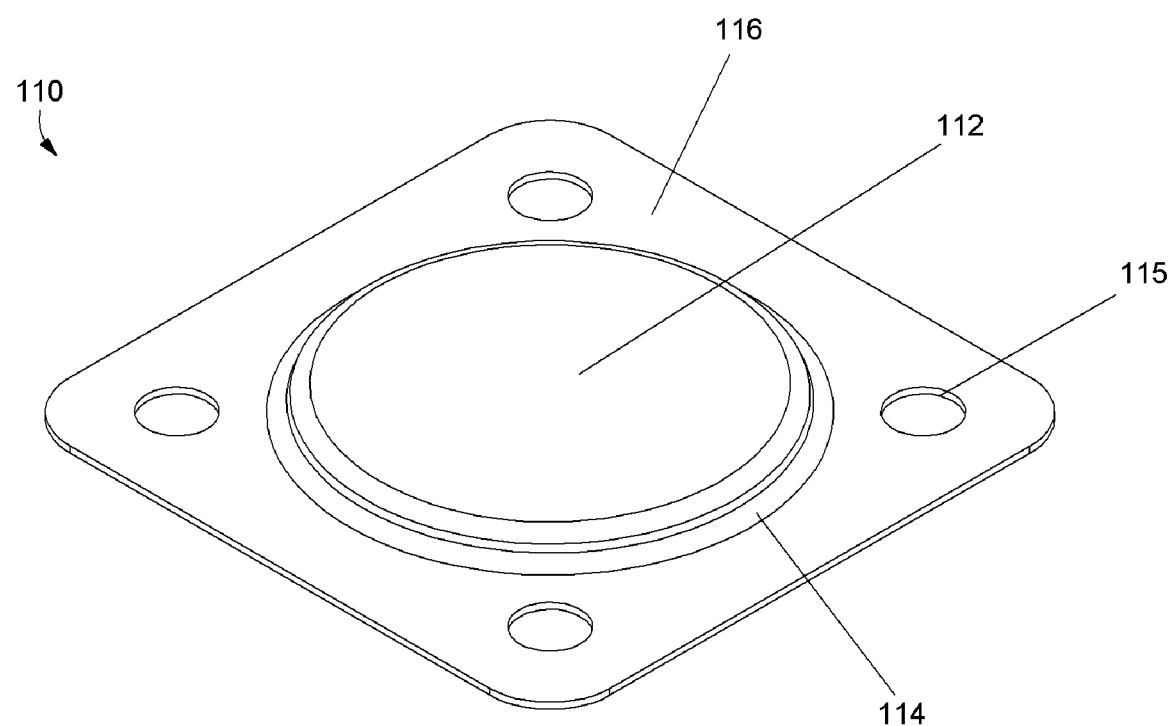
FIG. 4 is a top isometric view of an electrical contact according to an embodiment of the invention.

Referring also now to FIG. 4, a top isometric view of an electrical contact 110 according to an embodiment of the invention is shown. In one embodiment, a contact 110 may have a recessed side 113 and a protruding or protracted surface or side 112, which may be defined as a tissue contact or communication side. The presence of a protracted side 112 may enhance electrical coupling to tissue underlying the contact 110, thereby possibly reducing or avoiding problems such as unpredictable impedance and/or elevated power consumption. A protracted side 112 may have a planar surface, as illustrated, or may be angular in orientation relative to a periphery 116. A raised and/or sloping portion 114 may form a transition region between the protracted side 112 and the periphery 116.

The periphery 116 may contain a set of adhesive apertures 115 for facilitating bonding to the support member 120. Essentially any surgically suitable bonding material may be used to fuse a contact 110 to a support member 120 in an immovable, essentially immovable, or generally immovable manner. A lead wire 130 may be configured or adapted to couple the recessed underside 113 of the contact 110 to a pulse generator in a manner known to those of skill in the art. However, it should be appreciated by any artisan of ordinary skill in the art that a lead wire 130 may be electrically coupled to essentially any portion of an electrical contact 110, such as a protracted side 112 and/or a periphery 116.

In other embodiments, a contact's protracted side 112 may have other shapes and forms, and/or a raised portion 114 may be graduated or smoothly sloped. Although depicted as a substantially square shape with a circular contact surface 112, an electrical contact 110 may take essentially any shape found suitable for neural stimulation and/or monitoring. Moreover, depending upon embodiment details, one or more contacts 110 may have a tissue communication side that is level or essentially level with or below a surface of a support member 120. Electrical contacts 110, support members 120, and/or lead wires 130 may be constructed of materials such as those described in U.S. Patent Application Ser. No. 60/482,937, entitled "Apparatuses and Systems for Applying Electrical Stimulation to a Patient," incorporated herein by reference, and/or other suitable materials.

Figure 3C:
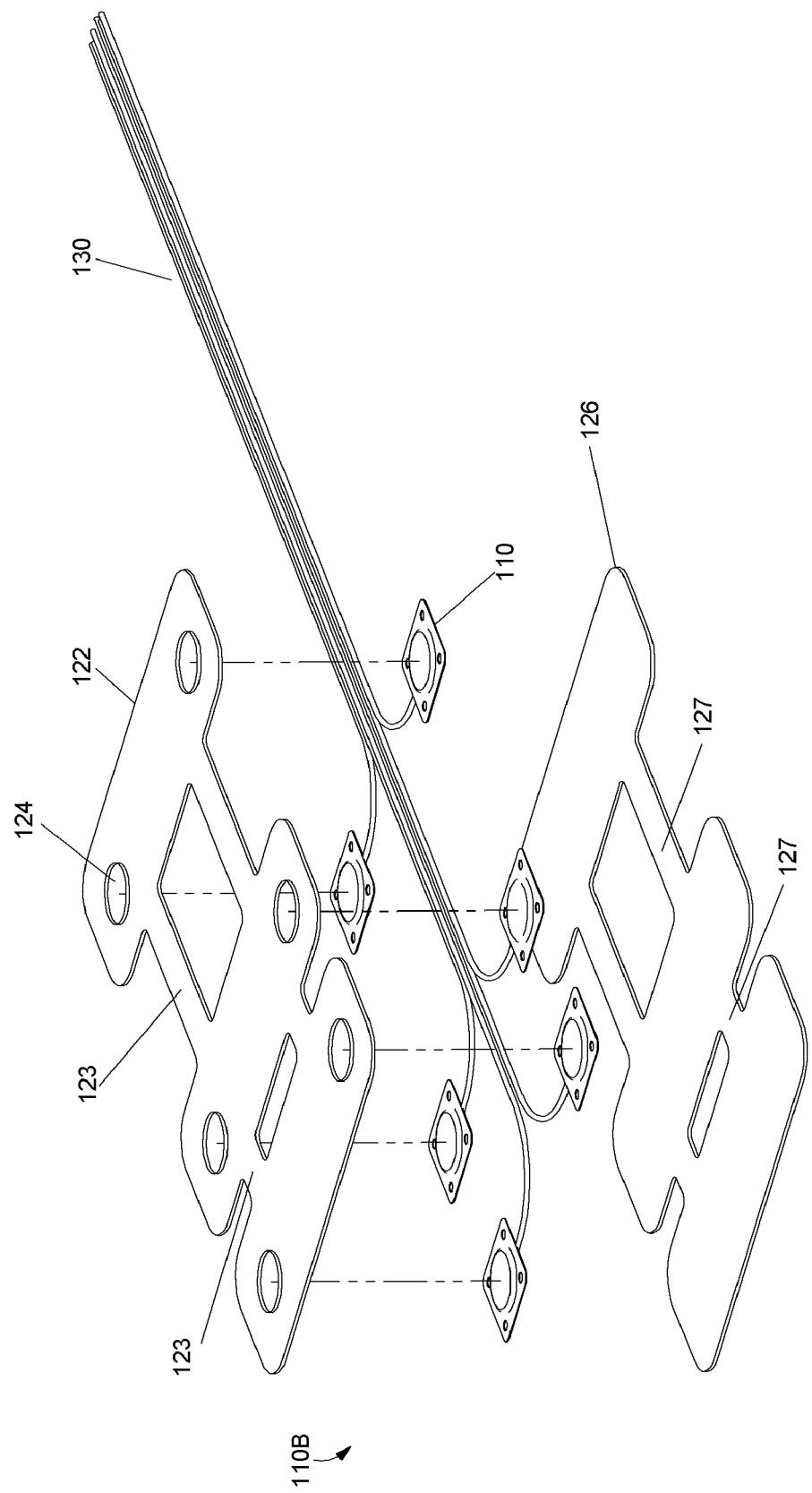
FIG. 3C is a partially exploded top isometric view of an articulated neural electrode assembly according to an embodiment of the invention.

FIG. 3C is a partially exploded top isometric view of an articulated neural electrode assembly 100B according to another embodiment of the invention. In one embodiment, a support member 120 may be comprised of an upper layer 122 and a lower layer 126, one or more portions of which may be of identical, essentially identical, or different thickness. Each such layer 122, 126 may be formed in accordance with a desired type of as-manufactured panel configuration. The upper and lower layers 122, 126 may be bonded together such that a set of electrical contacts 110 and a set of lead wires 130 reside between the upper and lower layers 122, 126. The upper layer 122 may have a plurality of contact apertures 124 which provide openings and/or conductivity conduits for the electrical contacts 110. A suitable bonding agent, such as a silicone adhesive, for example, can be applied between the two layers 122, 126 and then cured such that the two layers 122, 126 fuse into a single structure forming the support member 120. The protracted side 112 of an electrical contact 110 may at least partially extend above a contact aperture 124. A series of lead wires 130 is shown extending laterally from each of the electrical contacts 110 and similarly from the panels 105; however, it is to be noted that the lead wires 130 may also extend longitudinally from one or more electrical contacts 110 and/or panels 105, for example, in a manner identical or analogous to that shown in FIG. 3A.

In one embodiment, each of the upper and lower layers 122, 126 includes a set of preformed portions or segments 123, 127 for forming one or more coupling members 140. In such an embodiment, a coupling member 140 may comprise a segment 123 of the lower layer 122 bonded to a corresponding segment 127 of the upper layer 126, such that the bonded segments 123, 127 form a coupling member 140 that extends from one panel 105 to another. Preformed segments 123, 127 of the upper and/or lower layers 122, 126 may be thinner than the upper and/or lower layers 123, 127 themselves to facilitate ease of coupling member removal or detachment.

In an alternate embodiment, a support member 120 may comprise one layer (e.g., a lower layer 122) that includes a set of preformed portions or segments 123, 127; and a separate counterpart layer (e.g., a separate upper layer 126) corresponding to each panel 105, where each such counterpart layer lacks preformed portions or segments 123, 127. In yet another embodiment, each individual panel 105 may be independently formed from an upper and a lower layer 122, 126 that lack preformed segments 123, 127. Coupling members 140 may subsequently be formed between particular panels 105 through, for example, a molding and/or bonding procedure.

Figure 3D:
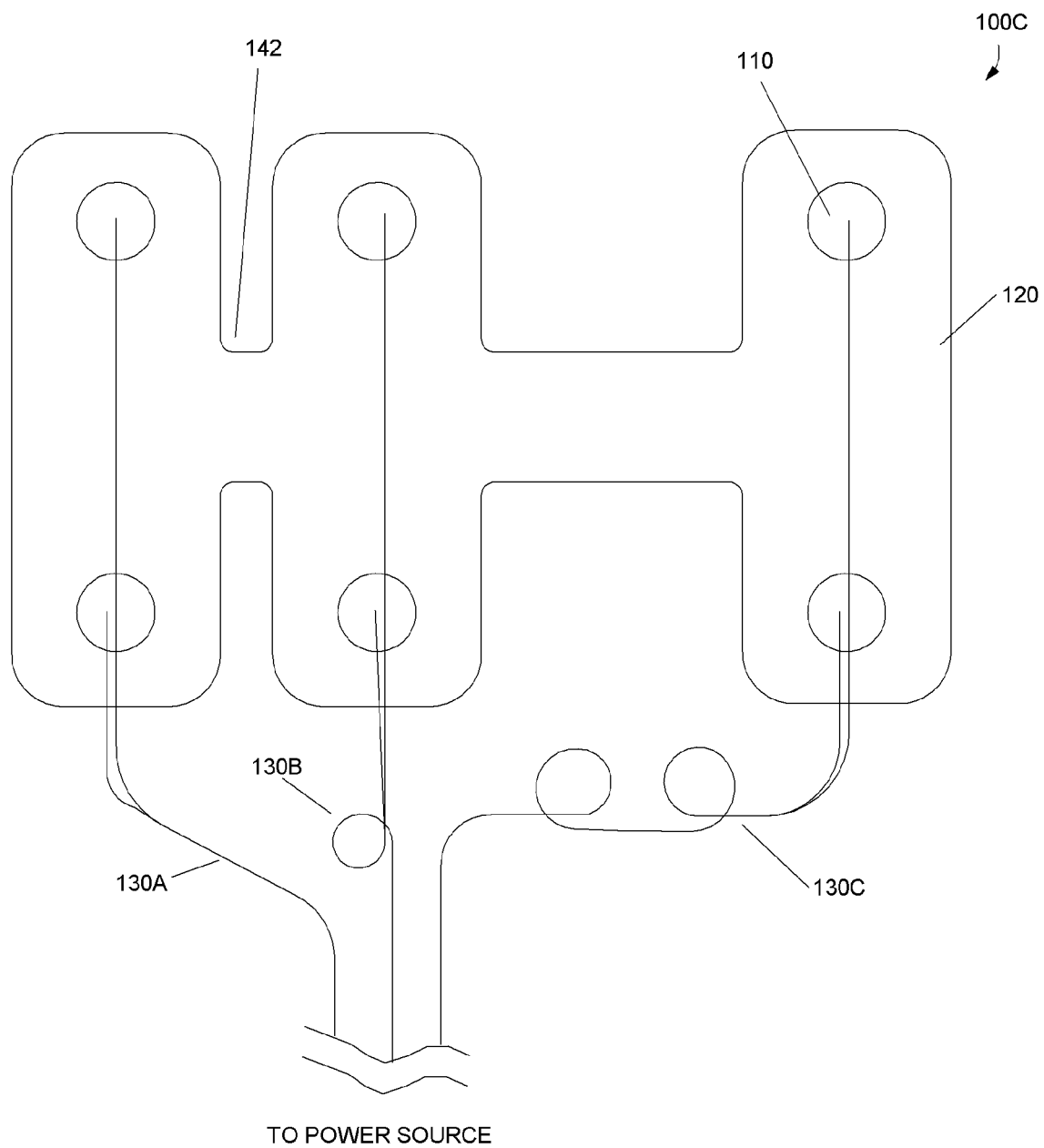
FIG. 3D is a plan view of an articulated neural electrode assembly according to another embodiment of the invention.

FIG. 3D is a plan view of an articulated neural electrode 100C according to another embodiment of the invention. In certain circumstances, ease of stimulation and/or monitoring of different neural locations (e.g., brain locations) may be enhanced through the use of lead wires 130 of different lengths. For example, a first lead wire 130a may be shorter than a second lead wire 130b and/or a third lead wire 130a. In such an embodiment, panels 105 may be selectively placed or deployed at variable distances with respect to one another. Different lead wire 130 lengths may provide flexibility in positioning electrical contacts 110 relative to stimulation and/or monitoring sites in different neural areas, which may possibly span different brain hemispheres.

Figure 3E:
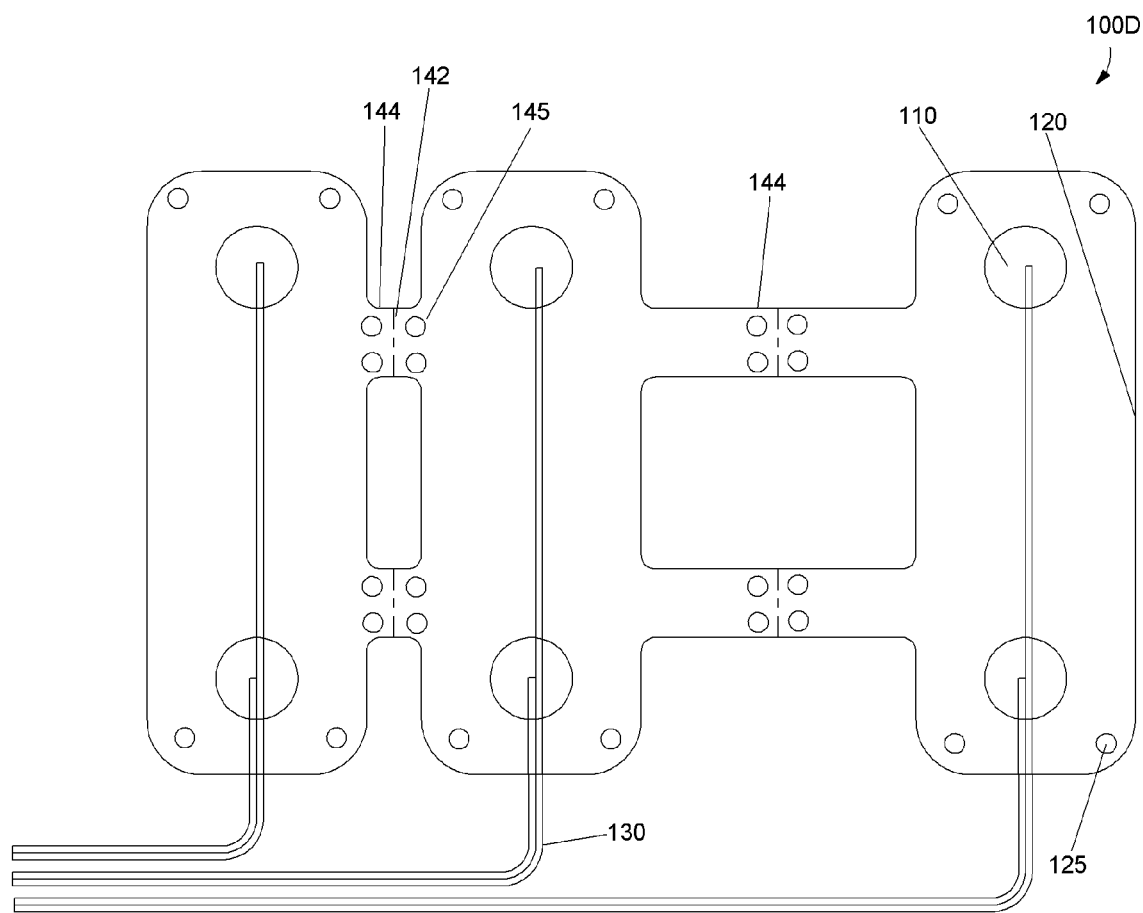
FIG. 3E is a plan view of an articulated neural electrode assembly according to another embodiment of the invention.

FIG. 3E is a plan view of an articulated neural electrode assembly 100D according to another embodiment of the invention. In one embodiment, one or more peripheral attachment apertures 125 may be provided or formed at or near a periphery of the support member 120. Additionally or alternatively, medial attachment apertures 145 may be provided upon or formed in one or more coupling members 140. Perforations 142 may facilitate ease of separation, decoupling, and/or detachment of said panels 105, and may be located approximately medially between said panels 105. In the embodiment shown, the coupling members 144 may be separated centrally, resulting in flap-like portions. A surgeon may thread sutures through some or all of said attachment apertures 125, 145 to anchor the articulated electrode assembly 100D to, for example, a patient's dura mater.

Figure 3F:
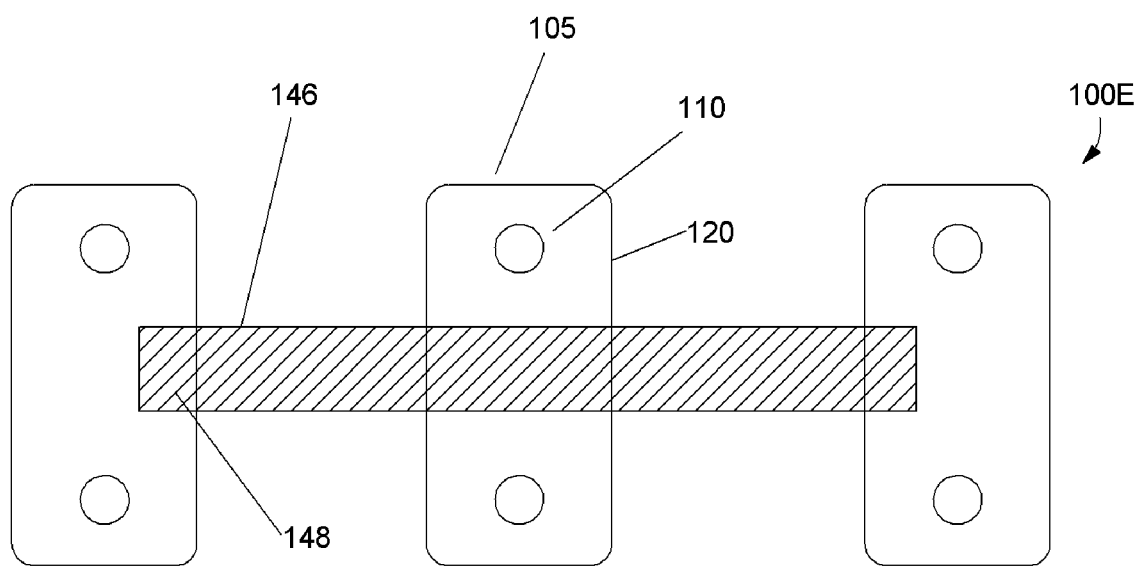
FIG. 3F is a plan view of an articulated neural electrode assembly according to yet another embodiment of the invention.

In another embodiment, panels 105 may be coupled in another manner, such as by a longitudinal strip 146 traversing each of the panels 105, as shown in FIG. 3F. The longitudinal strip 146 may be comprised of the same or similar surgically suitable material as a support member 120. The longitudinal strip 146 may be adhered and/or bonded to the exterior of either of an upper and/or lower layer 122, 126 of a support member 120, or at intersecting portions 148. Alternatively, the longitudinal strip 146 may be bonded or partially bonded to an interior portion of one or more panels 105. Bonding may be accomplished through the use of a silicone adhesive, for example, or any suitable bonding material known in the art. FIGS. 13A–13E are flowcharts describing procedures for manufacturing an articulated neural electrode assembly in accordance with various embodiments of the invention.

Figure 5:
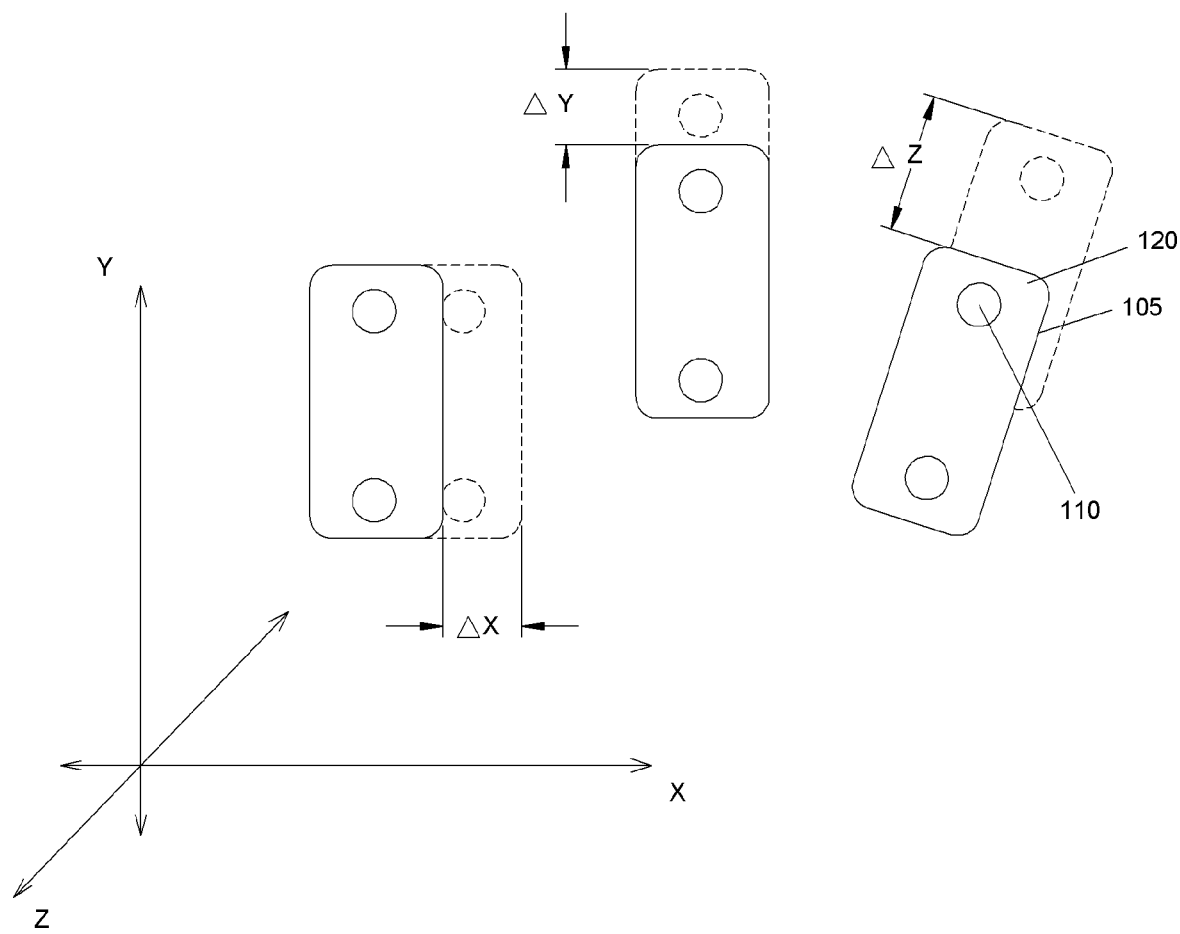
FIG. 5 is a schematic illustration showing exemplary spatially divergent orientations for portions of an articulated neural electrode assembly.

Various embodiments of articulated neural electrode assemblies 100 may be configured for spatially divergent placement of one or more panels 105 relative to one another at a set of stimulation and/or monitoring sites. FIG. 5 is an exemplary depiction of a set of panels 105a–c that are selectively positionable relative to one another along one or more of x, y, and z axes or directions and/or planes corresponding thereto. During a placement procedure, coupling members (not shown) may be removed, detached, or separated by a surgeon to facilitate panel placement relative to a set of stimulation sites. After such separation, an articulated electrode assembly 100 may be capable of signal transfer, exchange, or communication using an array of electrical contacts 110 that may be arranged or positioned in a multitude of possible orientations.

During procedures directed towards placing or positioning any given panel 105, minor displacements in one or more directions or planes may be desired. For example, if it is found or expected that neural stimulation efficacy is improved by displacing or repositioning a first panel 105a along an x axis from a first position (shown in phantom) to a second position, the change depicted by $\Delta x$, then such a displacement may be made. Likewise, placement of a second panel 105b may involve a shift along a y-axis from a first position (shown in phantom) to a second position, the change indicated by $\Delta y$. Similarly, a third panel 105c may be shifted from an initial position (phantom) to another position resulting in a $\Delta z$.

Referring again to FIG. 6, an articulated electrode assembly 100 can be placed in a multitude of desirable configurations upon or proximate to the brain and/or other neural tissue (e.g., the spinal cord). Configurable placement of one or more panels 105 may facilitate the generation of an intended or desirable electric field distribution. Although shown as implanted in one hemisphere, it is to be appreciated that a single articulated electrode 100 may have panels 105 implanted in both hemispheres. The spatially divergent structure of an articulated electrode assembly 100 may therefore facilitate various bilateral stimulation and/or monitoring capabilities. In such situations, multiple surgical openings may facilitate panel 105 implantation such that lead wires 130 are prevented from crossing or traversing particular anatomical structures, e.g., the interhemispheric fissure 55.

Figure 7A:
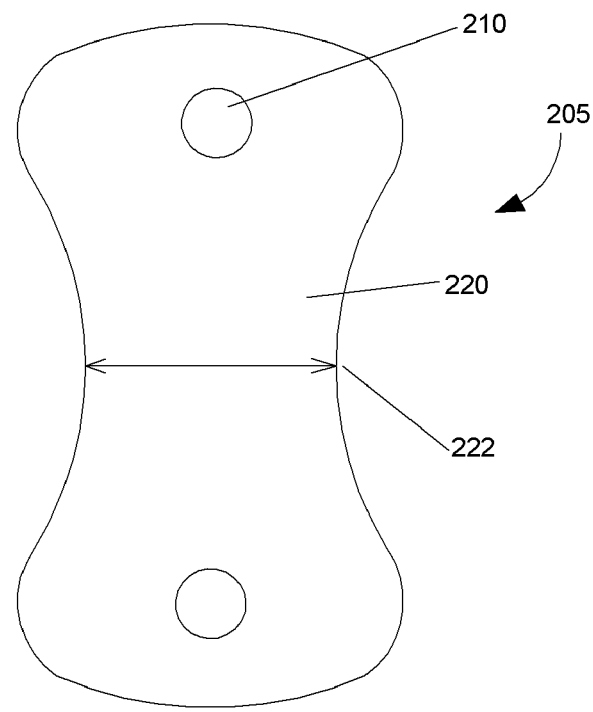
FIG. 7A is a plan view of an articulated neural electrode assembly panel according to an embodiment of the invention.
Figure 7B:
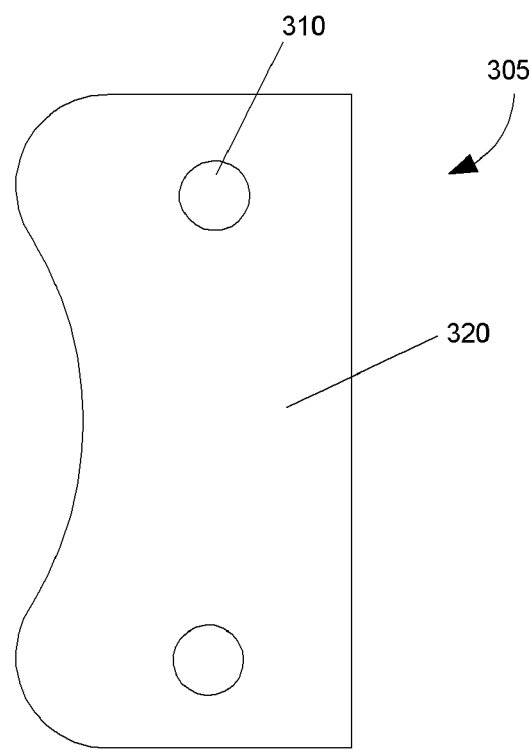
FIG. 7B is a plan view of another embodiment of an articulated neural electrode assembly panel.
Figure 8:
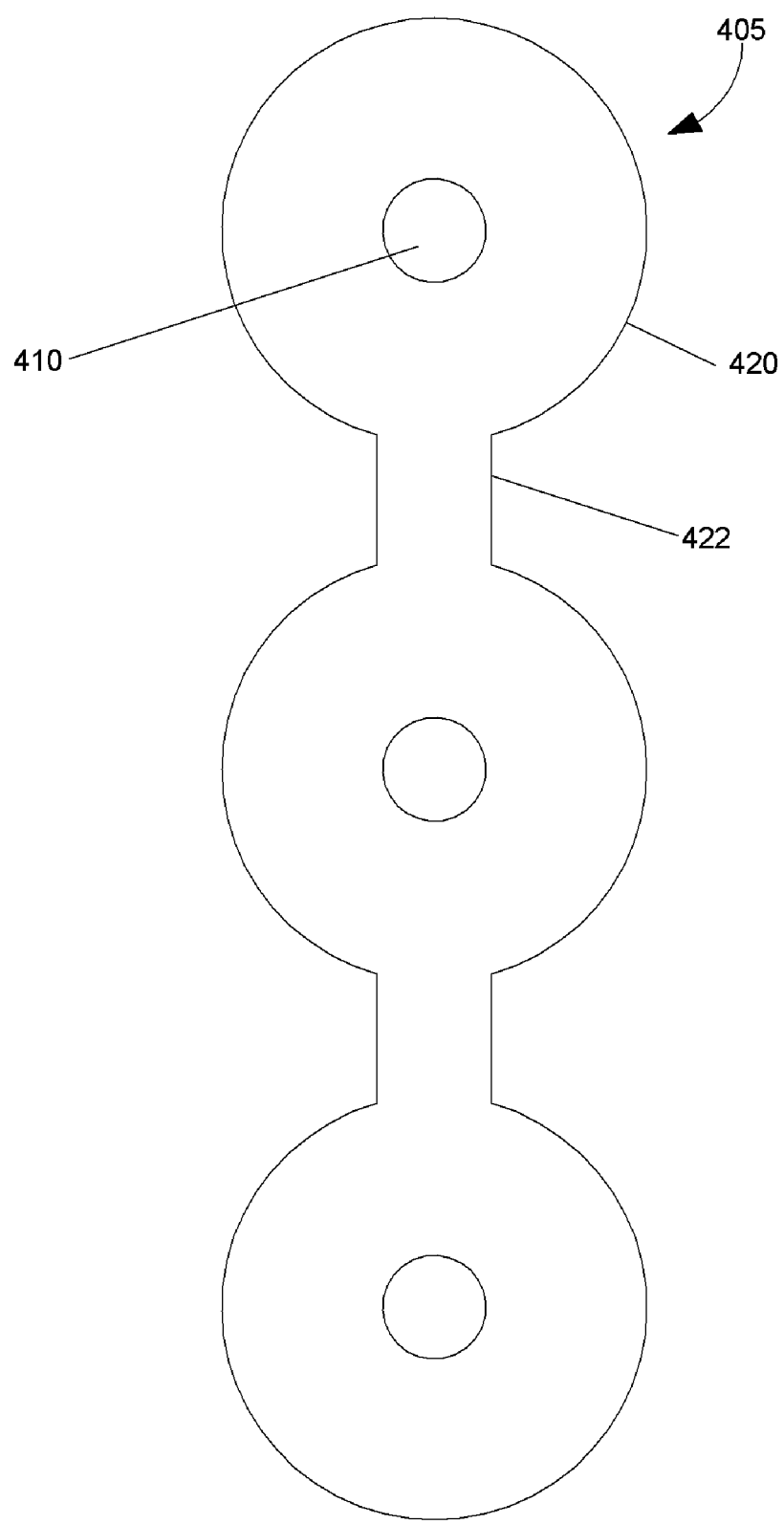
FIG. 8 is a plan view of another embodiment of an articulated neural electrode assembly panel.

An articulated electrode's panels 105 may be formed in any of several contoured shapes. FIGS. 7A, 7B and 8 illustrate examples of different shapes of panels 205, 305 and 405, respectively, according to particular embodiments of the invention. Although shown in a single form, it is to be understood that particular panels 205, 305, 405 may be coupled to adjacent or nearby panels 205, 305, 405 by one or more coupling members (not shown). In one embodiment as shown in FIG. 7A, a panel 205 has exemplary dimensions wherein a support member 220 may have a long or maximum length axis and at least one shortened, narrow, reduced, or minimum length axis. The presence of a shortened axis may form a waist portion 222. As shown in FIG. 7B, a panel 305 may have an asymmetric waist portion 322.

While FIG. 7A illustrates a panel 205 having a single waist portion 222, it is to be understood that a panel 405 may be configured, as illustrated in FIG. 8, as having multiple waist portions 422. Depending upon embodiment details, such a panel 405 may include multiple contacts 410 coupled to a single lead wire 130. Alternatively, one or more contacts 410 may be coupled to electrically distinct lead wires 130. In such an embodiment, a waist portion 422 may serve as a type of coupling member that facilitates separation and configurable placement of individual contacts 410 or contact sets associated with the panel 405.

Figure 9:
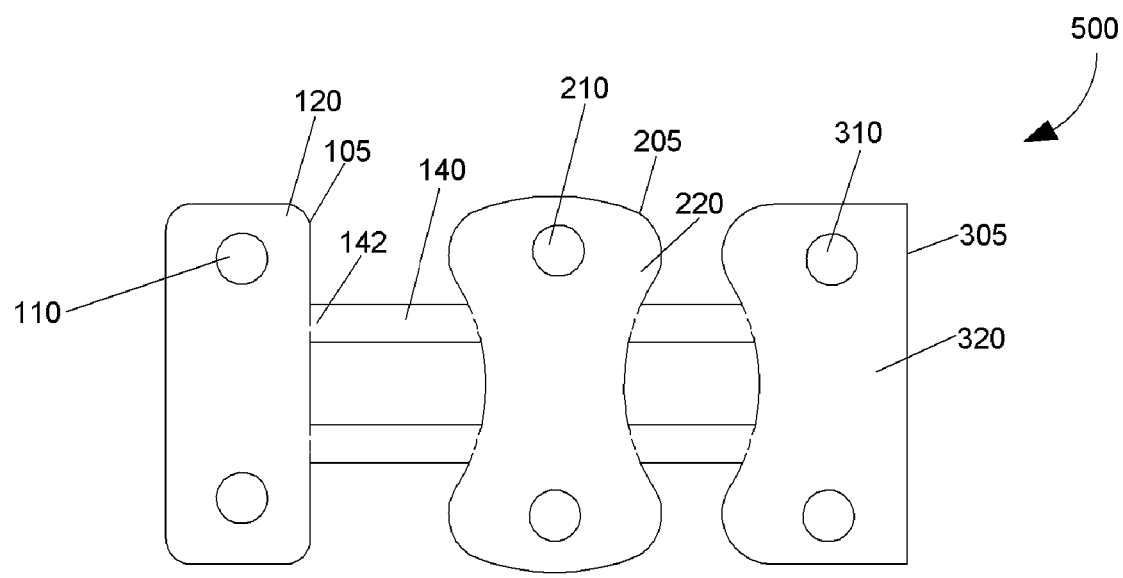
FIG. 9 is a plan view of an articulated neural electrode assembly comprising panels of different dimensions according to an embodiment of the present invention.

FIG. 9 is a plan view of an articulated neural electrode assembly 500 comprising panels 105, 205, 305 of different shapes, in accordance with another embodiment of the invention. An articulated electrode assembly 500 of the type shown in FIG. 9 may comprise one or more of a generally rectilinearly shaped panel 105, a spherically shaped panel 205, a plano-concave shaped panel 305, and/or one or more otherwise shaped panels.

Figure 10:
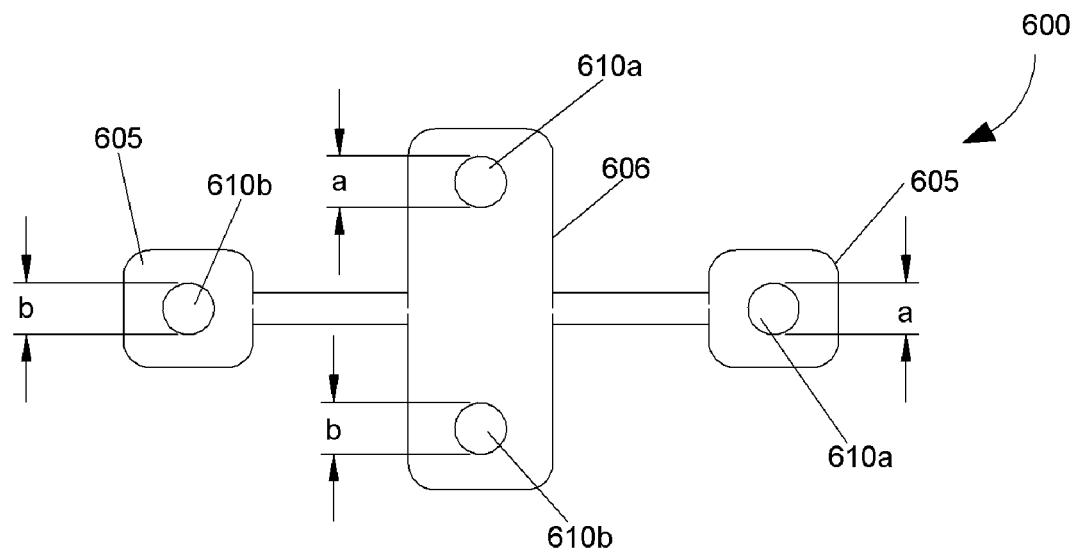
FIG. 10 is a plan view of an implantable articulated electrode assembly with panels of different dimensions and electrical contacts of different sizes according to an embodiment of the present invention.

FIG. 10 is a plan view of an articulated neural electrode assembly 600 according to another embodiment of the invention. In one embodiment, particular panels 605, 606 may be of different shapes and/or sizes, and/or one or more panels 605, 606 may carry a different number of and/or differently dimensioned electrical contacts 610a, 610b. For example, one contact 610a may be of a smaller diameter or area than another contact 610b. The use of panels 605, 606 that carry different numbers of electrical contacts 610a, 610b and/or differently dimensioned contacts 610a, 610b may aid panel placement procedures and/or impact neural stimulation and/or monitoring efficiency. For example, a larger-area contact 610b may facilitate more efficient delivery of larger magnitude stimulation signals that a smaller-area contact 610a. U.S. patent application Ser. No. 10/112,301, filed Mar. 28, 2002 entitled "Electrode Geometries for Efficient Neural Stimulation," provides a further discussion of the relationship between contact shape and electrical parameters, and is incorporated herein by reference. Altering contact dimension, panel dimension, and/or panel placement may optimize signal transfer, exchange, and/or communication into and/or through various neural structures and/or layers (e.g., cortical layers) associated with a stimulation and/or monitoring site.

Figure 11A:
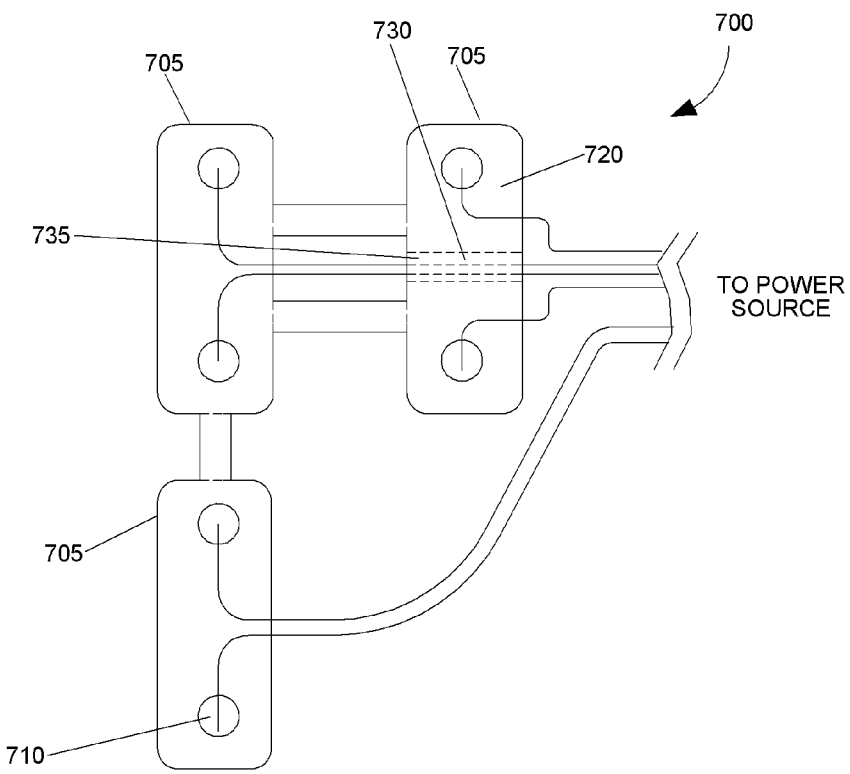
FIG. 11A is a schematic illustration of an articulated neural electrode assembly having a leadwire through-hole in a panel in accordance with an embodiment of the invention.
Figure 11B:
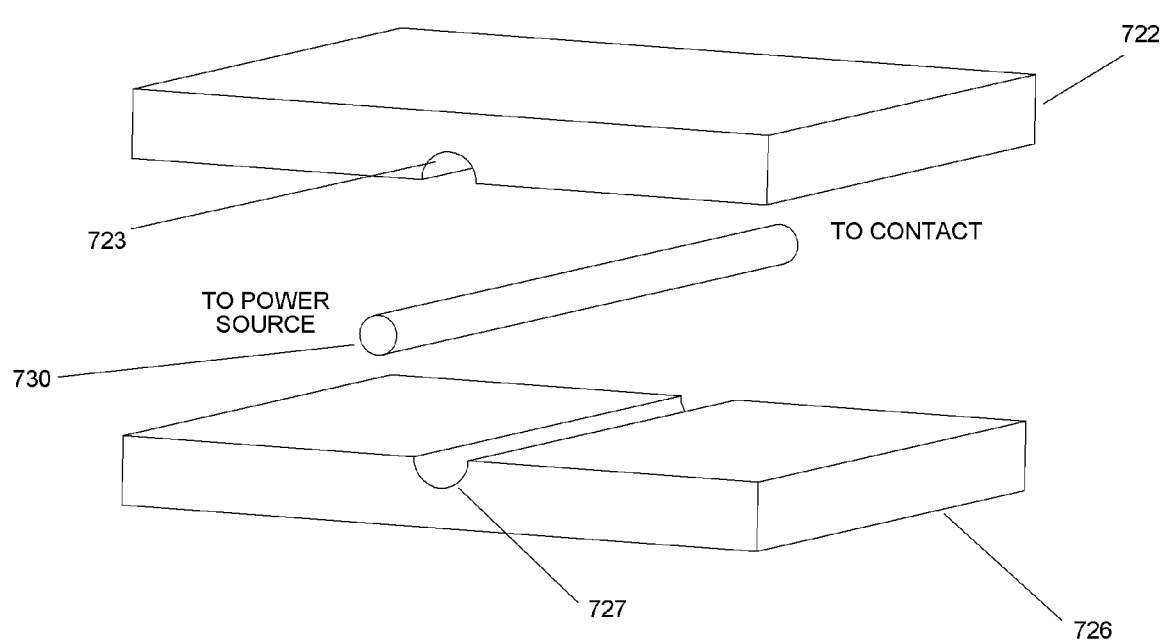
FIG. 11B is a partially exploded schematic illustration of the articulated neural electrode assembly of FIG. 11A.

FIG. 11A is a plan view and FIG. 11B is a partially exploded perspective view of an articulated neural electrode assembly 700 according to another embodiment of the invention. In certain embodiments, such as that depicted, a plurality of panels 705 need not be laterally placed relative to one another. One or more panels 705 may be placed in another orientation, for example, perpendicularly, relative to at least one other panel 705. In order to maintain panel placement flexibility, portions of one or more lead wires 730 may be slidably carried within a support member 720. In such an embodiment, a support member 720 may include a lead through-hole 735 formed therein. As shown more detail in FIG. 11B, in one embodiment, upper and lower support member layers 722 and 726, respectively, may each have matingly opposed grooves 723 and 727 therein that facilitate through-hole formation.

Figure 12:
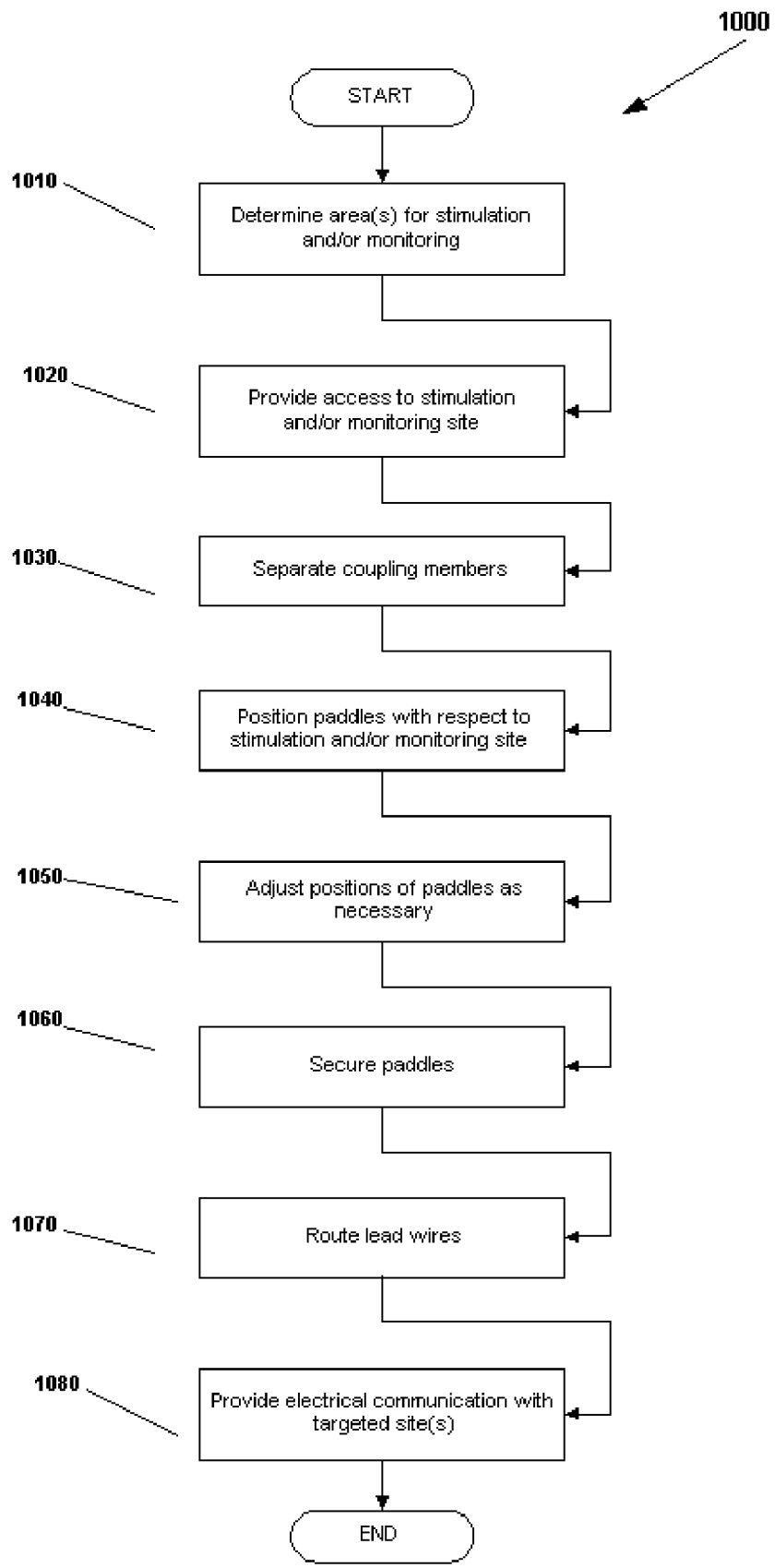
FIG. 12 is a flowchart illustrating an articulated neural electrode implantation, placement, and/or usage procedure according to an embodiment of the invention.
Figure 13A:
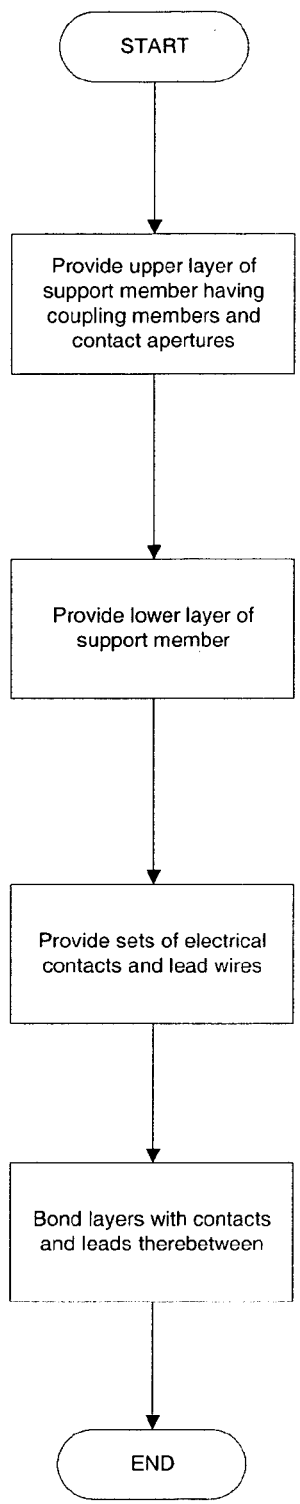
FIGS. 13A–13E are flowcharts describing procedures for manufacturing an articulated neural electrode assembly in accordance with various embodiments of the invention.
Figure 13B:
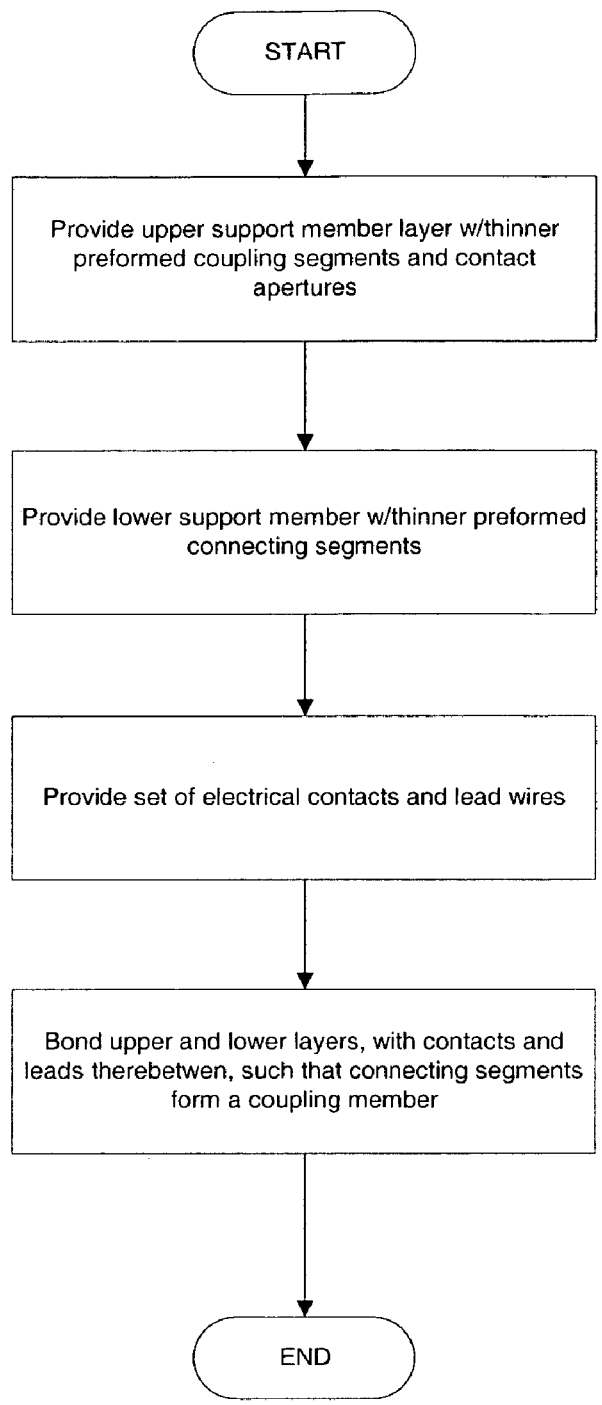
Figure 13C:
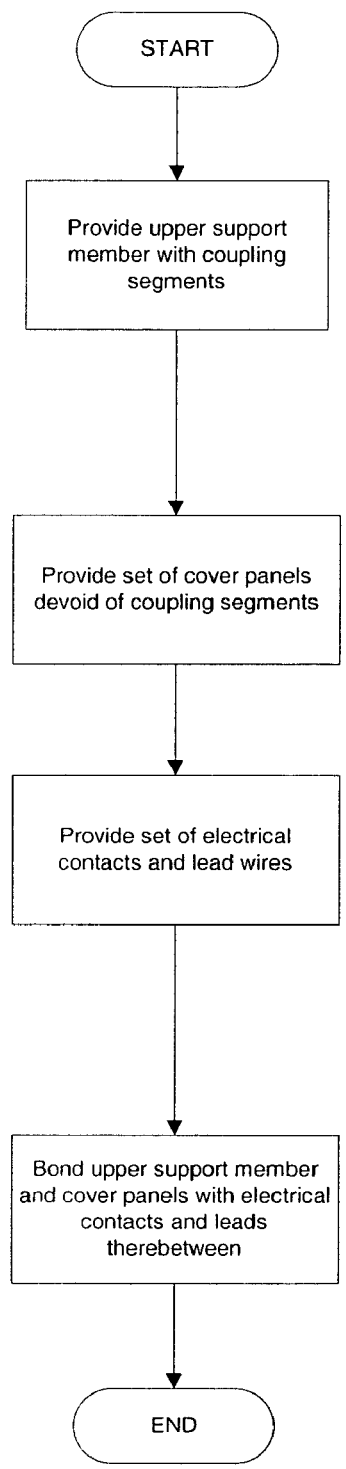
Figure 13D:
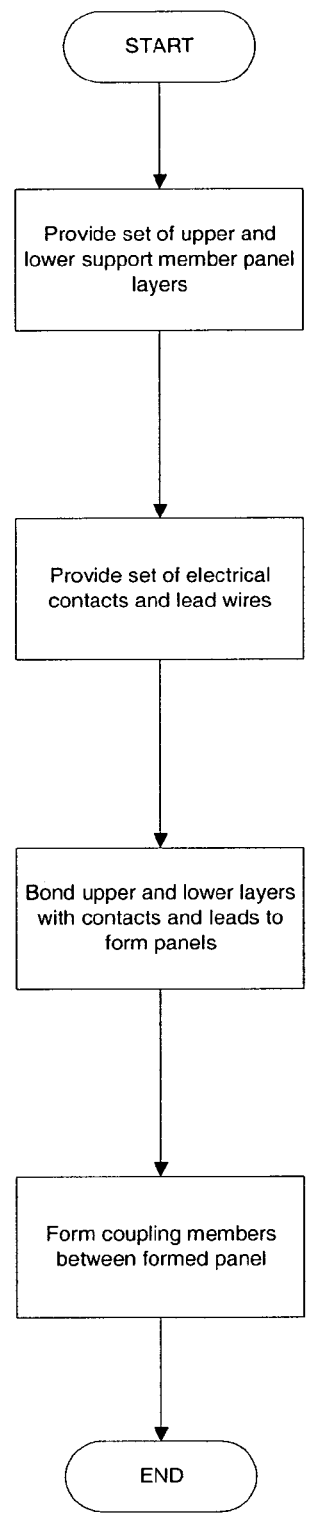
Figure 13E:
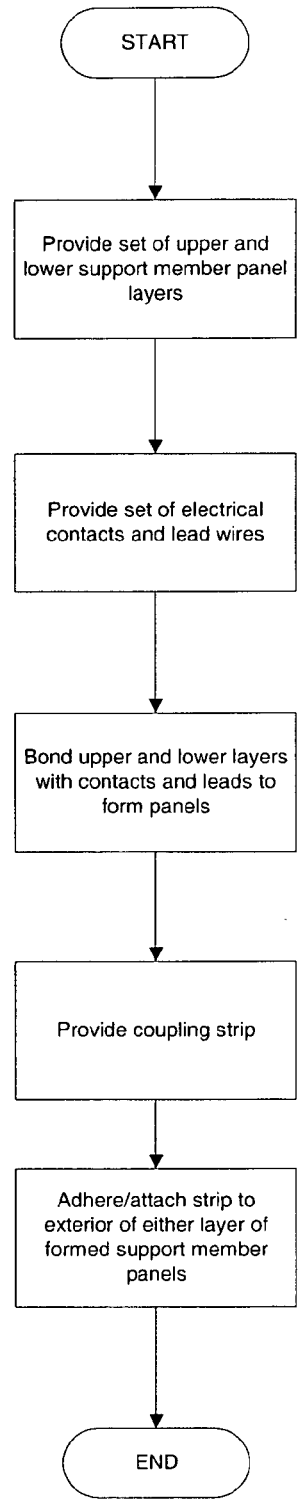

FIG. 12 is a flowchart illustrating an articulated neural electrode implantation, placement, and/or usage procedure 1000 according to an embodiment of the invention. Depending upon embodiment details, the description that follows may apply to essentially any articulated neural electrode embodiment in accordance with the invention, including one or more embodiments described above with reference to FIGS. 3A through 11B.

In one embodiment, the procedure 1000 comprises a site determination procedure 1010 that may involve identifying or determining a set of stimulation and/or monitoring sites at which one or more portions of an articulated neural electrode 100 may be implanted. Depending upon embodiment details, a site determination procedure 1010 may involve (1) identification of one or more anatomical landmarks; (2) preoperatively (for example, using Transcranial Magnetic Stimulation) and/or intraoperatively stimulating one or more neural locations to identify or map particular neural regions that induce or evoke a given type of patient response (for example, a movement or a sensation); (3) estimating a location at which the brain may recruit neurons to carry out a given type of neural activity that was previously performed by a damaged portion of the brain; (4) a neural imaging procedure; and/or (5) statistical considerations based upon one or more patient population samples.

A site determination procedure 1010 may additionally or alternatively involve the use of a neuronavigation system. With the aid of such a system, the anatomical location of particular stimulation and/or monitoring sites and neural tissue relevant thereto can be identified during surgical procedures. A neuronavigation system may comprise stereotactic surgical equipment that may be used to determine the precise relationship between surgical instruments and anatomical structures, in a manner understood by those skilled in the art.

Certain manners of identifying stimulation sites are detailed in U.S. application Ser. No. 09/802,808, entitled "Methods and Apparatus for Effectuating a Lasting Change in a Neural Function of a Patient," which is incorporated herein by reference. In general, the number and/or location of stimulation and/or monitoring sites under consideration may depend upon the nature, number, and/or extent of a patient's neurological condition and/or functional deficits.

An articulated neural electrode implantation, placement, and/or usage procedure 1000 may additionally include an access procedure 1020 that involves accessing one or more stimulation and/or monitoring sites. An accessing procedure 1020 may rely upon surgical techniques, for example, performing a craniotomy and/or forming one or more burr holes in the patient's skull.

The procedure 1000 may further include a separation procedure 1030 that involves separating, detaching, decoupling, and/or removing coupling members 140 that couple an articulated electrode's panels 105, possibly in a selective manner. Once separated, panels 105 may be available for spatially divergent placement relative to one another and/or a set of stimulation and/or monitoring sites.

An articulated electrode implantation, placement, and/or usage procedure 1000 may also include a placement procedure 1040. In one embodiment, a placement procedure 1040 involves a general placement or positioning of one or more panels 105 at particular stimulation and/or monitoring sites. A placement procedure 1040 may alternatively or additionally involve specific placement, positional adjustment, and/or positional readjustment of one or more panels 105 relative to given stimulation and/or monitoring sites. In certain embodiments, a more specific placement may involve fine adjustments in one or more of an x, y, and/or z direction and/or planes corresponding thereto. A specific placement may involve maneuvering a panel 105 such that electrical contacts 110 carried thereby are positioned in a desired manner relative to a stimulation and/or monitoring site, possibly based upon neural topography. A procedure 1000 may further include an anchoring procedure 1060 that involves securing particular portions of one or more panels 105 to a stimulation and/or monitoring site, for example, through the use of sutures.

A procedure 1000 may additionally include a lead wire placement procedure 1070, which may involve routing lead wires 130 in and/or around tissues between an articulated electrode assembly 100 and a pulse generator 150. A lead wire placement procedure 1070 may involve a surgical tunneling procedure that facilitates routing lead wires 130 between a subclavicular region, along the back of the neck, and around a portion of a patient's skull 57 (FIG. 6).

An articulated neural electrode implantation, placement, and/or usage procedure 1000 may also include a stimulation procedure 1080 and/or a monitoring procedure 1082. In a stimulation procedure 1080, electrical energy may be supplied to one or more panels 105 or electrical contacts 110 of an articulated electrode assembly 100 to provide, apply, or deliver electrical energy at or proximate to one or more stimulation sites. Depending upon embodiment details, electrical energy may be applied to panels 105 in a simultaneous, sequential, or pseudo-random manner. In a monitoring procedure 1082, one or more panels 105 or electrical contacts 110 may be used to detect neuroelectric activity at or proximate to one or more monitoring sites.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. An articulated electrode assembly, said assembly comprising:
   at least three electrode paddles, each electrode paddle positioned adjacent another electrode paddle and comprising:
   a support member;
   a set of electrical contacts carried by said support member for contacting a patient; and
   an electrical lead wire at least partially carried by said support member and coupled to at least one electrical contact; and
   at least one coupling member positioned between each set of adjacent sides of said at least three electrode paddles and having a narrowed portion relative to said adjacent sides so as to aid in the decoupling of said electrode paddles from one another wherein said electrical wires carried by said support members are of different lengths relative to one another thereby facilitating different spacing between the electrode paddles when uncoupled.

2. The articulated electrode assembly of claim 1, wherein at least one coupling member is substantially smaller in volume than at least one paddle.

3. The articulated electrode assembly of claim 1, wherein the support member has at least one layer is configured with
   a set of recesses for supporting the at least one electrical contact, and at least one support member layer is substantially flexible,
   said at least one layer having at least one contact aperture formed therein, the at least one aperture facilitating electrical conductivity.

4. The articulated electrode assembly of claim 3, wherein at least one support member layer is configured to have a contoured shape.

5. The articulated electrode assembly of claim 1, wherein a subset of the electrical contacts comprises a single formed structure having a first tissue contact side.

6. The articulated electrode assembly of claim 1, wherein at least one support member has a major axis and a minor axis of different dimensions.

7. The articulated electrode assembly of claim 6, wherein the minor axis has at least one recessed waist portion.

8. The articulated electrode assembly of claim 1, wherein each of the support members is comprised of an upper and lower layer of material,
   and wherein the set of stimulation paddles comprises at least two paddles,
   and wherein each of the upper and lower layers has a conduit formed therein, and
   wherein each of the conduits matingly oppose one another, forming a passageway to carry a portion of the electrical lead wire.

9. The articulated electrode assembly of claim 1, wherein the support member of at least one of the paddles is of a different dimension than the support member of another paddle.

10. The articulated electrode assembly of claim 1, wherein
    the set of electrical contacts comprises at least two electrical contacts having different dimensions.

11. The articulated electrode assembly of claim 1, wherein said support member is configured to allow at least partial exposure of said set of electrical contacts for electrical communication at a neuroanatomical site.

12. The articulated electrode assembly of claim 1, wherein
    the coupling member is configured to couple the set of paddles in a fixed spatial relationship, and
    wherein the coupling member includes at least one detachment portion that facilitates detachment of the first and second paddles from each other.

13. The articulated electrode assembly of claim 12, wherein
    the coupling member has a separation mechanism configured for separable coupling to another paddle, and
    wherein at least one of said coupling members is physically decouplable with the separation mechanism.

14. The articulated electrode assembly of claim 13, wherein
    the separation mechanism comprises at least one perforation.

15. The articulated electrode assembly of claim 13, wherein
    said coupling member comprises a contiguous strip.

16. An articulated electrode assembly, said assembly comprising:

a set of paddles, each paddle positioned adjacent another electrode paddle and comprising:

a support member;

a set of electrical contacts carried by the support member for contacting a patient; and a set of electrical leads comprising at least one electrical lead wire, each electrical lead wire being coupled to an electrical contact, and each electrical lead wire at least partially carried by at least one support member at least one coupling member positioned between adjacent sides of said set of paddles and holding said set of paddles spaced from one another, said coupling member being narrower in dimension than said adjacent paddles sides and having a perforated portion.

17. The articulated electrode assembly of claim 16, wherein at least two of the electrical lead wires have a different length.

18. The articulated electrode assembly of claim 16, wherein at least one electrical lead has at least one visible indicator corresponding to its length.

19. The articulated electrode assembly of claim 16, wherein the at least one coupling member includes at least one attachment aperture.

20. An implantable electrical system, said system comprising:

(a) an articulated electrode assembly, said assembly comprising:

at least three electrode paddles, each electrode paddle positioned adjacent another paddle and comprising;

a support member;

a set of electrical contacts carried by said support member for contacting a patient; and at least one coupling member positioned between each set of adjacent sides of said at least three electrode paddles and having a narrowed portion relative to said adjacent sides so as to aid in the decoupling of said electrode paddles from one another; and (b) a pulse generating device; and (c) a set of lead wires, each wire of said set at least partially carried by one of said support members and coupling at least one electrical contact of each paddle to said pulse generating device, wherein said electrical wires carried by said support members are of different lengths relative to one another thereby facilitating different spacing between electrode paddles when uncoupled;

(d) wherein said articulated electrode assembly, pulse generating device and set of lead wires are dimensioned and configured for implantation within a patient and comprised of biocompatible materials.

21. A method for implanting a neural electrode assembly within a patient, said method comprising:

determining a set of neural target sites;

providing access to said target sites;

physically decoupling a set of coupling members spanning between a set of paddles whereby said decoupling provides for paddle detachment and separation from each other; said paddles having a set of electrical contacts; and implanting each of said paddles relative to the target sites.

22. The method of claim 21, further comprising:

spatially adjusting an orientation of said paddles; and providing electrical communication with said target site via said set of electrical contacts.

23. The method of claim 21, wherein said physically decoupling step comprises one from the group of detaching and dividing said coupling members.

24. The method of claim 21, wherein said placing step comprises placing said paddles at a set of neuroanatomical sites.

25. The method of claim 24, wherein at least one neuroanatomical site comprises one from the group of an epidural and a subdural site.

26. The method of claim 21, wherein said providing step comprises providing surgical access to an implantation target site, and said providing surgical access step comprises performing one from the group of an incision, a craniotomy, and a burr hole procedure.

* * * * *